(12) United States Patent
Hageman et al.

(10) Patent No.: US 11,457,657 B2
(45) Date of Patent: Oct. 4, 2022

(54) TREATMENT OF TRAUMATIC BRAIN INJURY

(71) Applicant: N.V. Nutricia, Zoetermeer (NL)

(72) Inventors: Robert Johan Joseph Hageman, Utrecht (NL); Ladislaus Maria Broersen, Utrecht (NL); Nick Van Wijk, Utrecht (NL)

(73) Assignee: N.V. Nutricia, Zoetermeer (NL)

( * ) Notice: Subject to any disclaimer, the term of this patent is extended or adjusted under 35 U.S.C. 154(b) by 49 days.

(21) Appl. No.: 16/739,601

(22) Filed: Jan. 10, 2020

(65) Prior Publication Data

US 2020/0146326 A1    May 14, 2020

Related U.S. Application Data

(63) Continuation of application No. PCT/NL2018/050475, filed on Jul. 12, 2018.

(30) Foreign Application Priority Data

Jul. 12, 2017   (WO) ................ PCT/NL2017/050468

(51) Int. Cl.
*A23L 33/17* (2016.01)
*A23L 33/115* (2016.01)
*A23L 33/125* (2016.01)

(52) U.S. Cl.
CPC ........... *A23L 33/115* (2016.08); *A23L 33/125* (2016.08); *A23L 33/17* (2016.08)

(58) Field of Classification Search
None
See application file for complete search history.

(56) References Cited

U.S. PATENT DOCUMENTS

2014/0256813 A1   9/2014 Opheim

FOREIGN PATENT DOCUMENTS

| CN | 103371993 A | 10/2013 | | |
|---|---|---|---|---|
| WO | WO-2006/118665 A2 | 11/2006 | | |
| WO | WO 2012/113415 | * 8/2012 | ............... | A23L 1/29 |
| WO | WO-2012/113415 A1 | 8/2012 | | |
| WO | WO-2012/125034 A1 | 9/2012 | | |
| WO | WO 2014/027015 | * 2/2014 | ............... | A23L 1/29 |
| WO | WO-2015/034812 A2 | 3/2015 | | |
| WO | WO-2015/115885 A1 | 8/2015 | | |
| WO | WO 2015/156865 | * 10/2015 | ............. | A61K 31/22 |
| WO | WO-2019/013615 A1 | 1/2019 | | |

OTHER PUBLICATIONS

Healthline (available online at https://www.healthline.com/nutrition/mct-oil-vs-coconut-oil, accessed Apr. 23, 2021) (Year: 2021).*
Cristofori et al., White and gray matter contributions to executive function recovery after traumatic brain injury, American Academy of Neurology, vol. 84, Apr. 7, 2015, 8 pages.
International Search Report and Written Opinion for International Application No. PCT/NL2017/050467, dated Mar. 22, 2018, 10 pages.
International Search Report and Written Opinion for International Application No. PCT/NL2017/050468, dated Mar. 23, 2018, 10 pages.
International Search Report and Written Opinion for International Application No. PCT/NL2018/050475, dated Oct. 11, 2018, 10 pages.
Prins et al., The collective therapeutic potential of cerebral ketone metabolism in traumatic brain injury, Journal of Lipid Research, vol. 55, published Apr. 8, 2014, 8 pages.

* cited by examiner

*Primary Examiner* — Craig D Ricci
(74) *Attorney, Agent, or Firm* — N.V. Nederlandsch Octrooibureau; Catherine A. Shultz; Tamara C. Stegmann

(57) ABSTRACT

The invention provides for an enteral nutritional composition comprising (a) a lipid fraction, (b) a digestible carbohydrate fraction and (c) a protein fraction, wherein the lipid fraction comprises therapeutically effective amounts of (i) DHA and optionally EPA, and (ii) medium-chain triglycerides, preferably at least 2 wt % C8 and C10 medium-chain triglycerides based on weight of the fatty acids; and wherein the composition has a ketogenic weight ratio between 1.4:1 and 3:1, for use in the treatment of traumatic brain injury (TBI).

12 Claims, 6 Drawing Sheets

TREATMENT OF TRAUMATIC BRAIN INJURY

CROSS REFERENCE TO RELATED APPLICATIONS

Figure 1:
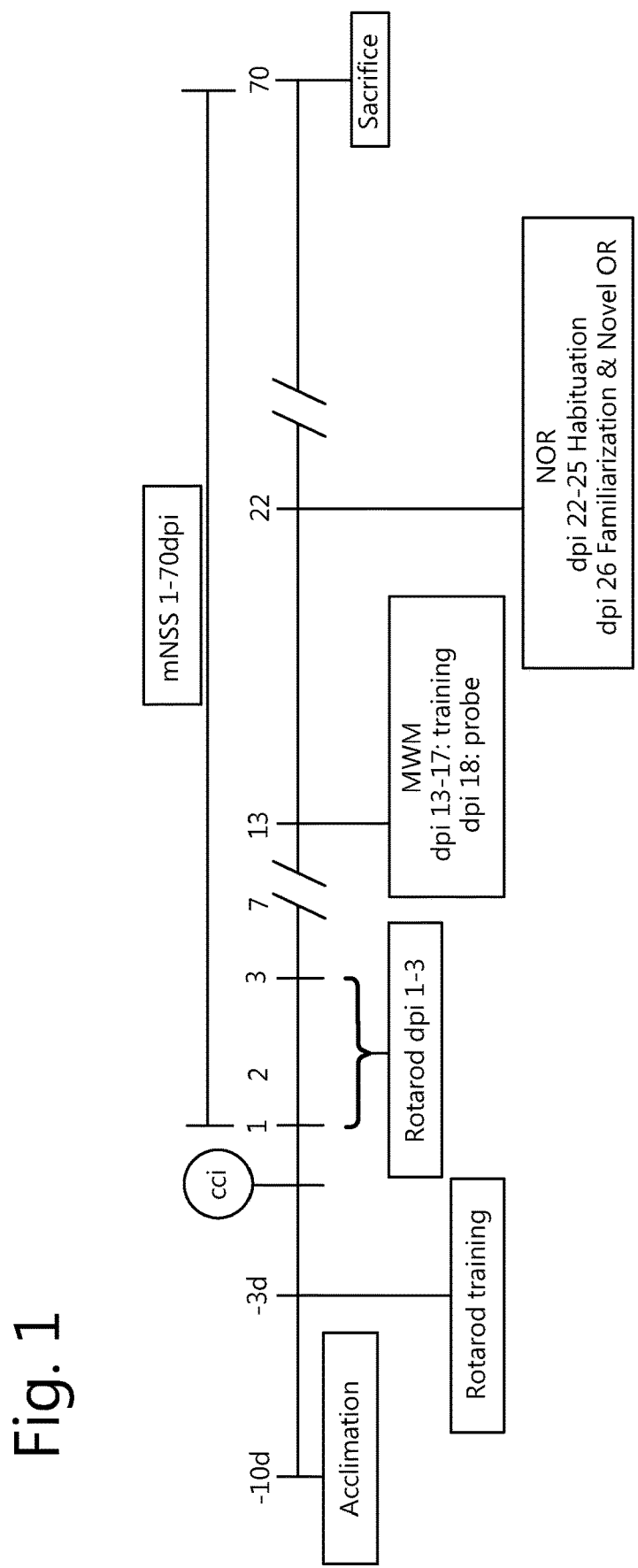

This application is a continuation of International Application No. PCT/NL2018/050475, filed on Jul. 12, 2018, which claims the benefit of and priority to International Application No. PCT/NL2017/050468, filed Jul. 12, 2017, both of which are hereby incorporated by reference herein in their entireties.

FIELD OF THE INVENTION

The present invention is in the field of medical nutrition and more particularly relates to nutritional compositions for use in the treatment of and recovery from traumatic brain injury and the symptoms associated with it.

BACKGROUND TO THE INVENTION

Traumatic brain injury (TBI) is a form of acquired brain injury. TBI is a serious medical condition that may occur after the brain is subjected to a significant external physical impact. TBI is the leading cause of disability and death in people under 45 with approximately 10 million new cases each year worldwide.

According to the diagnostic criteria detailed in the "Diagnostic and Statistical Manual of Mental Disorders (DSM-5) TBI has one or more of the following characteristics: changes in levels of consciousness; memory disturbances; confusion associated with deficits in orientation; neurological signs, such as brain injury observed on neuroimaging, new onset or worsening of seizure disorder, visual field deficits and hemiparesis. While some symptoms may appear immediately after the injury, others may evolve over time consistent with anatomical changes in the neural substrates following the injury.

The primary phase of TBI describes immediate brain tissue damage from contusions or oxygen deprivation caused by global mass effect. The primary injury in TBI can only be reduced through improved prevention. Secondary injury starts after trauma and underlies the functional deficits associated with TBI. It occurs later via such mechanisms as reperfusion injury, delayed cortical edema, blood-brain barrier (BBB) breakdown, glutaminergic overexcitation and local electrolyte imbalance. These disturbances themselves result in reactive oxygen species (ROS)-mediated neurodegeneration through calcium release, glutamate toxicity, lipid peroxidation, and mitochondrial dysfunction. Such secondary injury may occur in brain adjacent to the site of initial supposed injury, yielding the potential for unexpected spread of the zone of damage over months post-injury. Presently, there are no treatments to counter such adverse outcomes. Thus, developing efficacious therapeutic interventions to protect the brain and promote repair after TBI is a particularly urgent pursuit.

TBI survivors can experience a wide range of deficits, and sensorimotor as well as cognitive impairment is a common consequence of this injury. Sensorimotor impairment includes elements of paresis, postural imbalance and gait disturbance, and early acute disruption of the startle reflexes. TBI can result in to bradykinesia, abnormal sway and an impaired reaction time. Early balance impairment is a predictor of worse outcome post-TBI. Sensorimotor problems may improve over time, although depending on severity deficits may persist beyond the first 1-2 years after trauma. In cognitive domains, impairments are observed in memory, attention and information processing speed, with more severe TBI causing greater and longer-lasting deficits than mild or moderate TBI. Adequate treatment for TBI to prevent these long-term effects is not yet available.

Many lipid blends have been used in the manufacture of foods for improving brain function. Immediate (intravenous) infusion of large quantities of DHA directly after the TBI event can decrease the adverse effects of TBI on brain function in animal models. It is believed that only minor amounts of DHA enter the brain per day and that any supplementation of DHA can only be useful when it is administered within a few hours after the event.

WO2006/118665 discloses a method of reducing protein aggregation in the brain of a mammal by increasing endogenous ketone levels using a so-called ketogenic diet. TBI patients who were fasted or maintained on a ketogenic-like diet to minimize hyperglycaemia showed significantly lower plasma glucose and lactate concentrations, elevated β-hydroxybutyrate levels and better urinary nitrogen balance compared to standard fed patients.

The ketogenic diet (KD) is thought to result in adaptive changes to brain energy metabolism that increase the energy reserves. This is believed to help the neurons to remain stable in the face of increased energy demand, and may confer a neuroprotective effect. In the ketogenic diet, carbohydrate levels are restricted. Classical ketogenic diets comprise an amount of lipids (weight), which is about 4-fold the weight of the sum of proteins and digestible carbohydrates. Fatty acids are used as the major source of fuel. These are used through fatty-acid oxidation in the cell's mitochondria. The brain is normally fueled solely by glucose, lipids in the form of plasma lipoproteins as such do not cross the blood-brain barrier to a substantial degree. The liver can use long-chain fatty acids though to synthesise the three ketone bodies β-hydroxybutyrate, acetoacetate and acetone. These ketone bodies can under conditions enter the brain and act as a glucose substitute. Additionally medium-chain fatty acids octanoic (C8) and heptanoic (C7) acids can cross the blood brain barrier and be used by the brain. When glucose and ketone bodies are simultaneously present to neurons, glucose will by far be the preferred energy source. That is why the classical ketogenic diet has a large excess of lipids and hardly any digestible carbohydrates. Typically the degree of ketogenicity decreases considerably when the amount of digestible carbohydrates in the diet is increased.

The Medium Chain Triglyceride Ketogenic Diet (MCTKD) is a variant thereof. The original MCT diet developed in the 1970s derived 60% of its calories from MCT oil. Moreover, consuming such a quantity of MCT oil causes abdominal cramps, diarrhoea and vomiting though, which is a severe drawback for its use. The diet is, like the ketogenic diet, unpalatable which makes it difficult to adhere with. In addition, the health consequences of a very high fat diet for life can be considerable.

The Low Glycemic Index Diet is another variant. The glycemic index classifies carbohydrates by their potential to raise blood glucose on a scale from 0-100. The low glycemic index diet allows for a greater intake of digestible carbohydrates but the carbohydrates are limited to those with a low glycemic index (typically considered a glycemic index of 55 or less). In practice low GI nourishment does not induce a ketogenic state and people find the diet often difficult to adhere to.

The Modified Atkins Diet (MAD) is another, more liberal variation of the traditional ketogenic diet mainly limited in the amount of digestible carbohydrates. While the ketogenic diet is typically given at 4:1 or 3:1 ketogenic ratio, which is the ratio of the amount of fat to the combined amounts of protein and digestible carbohydrates, MAD involves about a 1:1 ratio, which allows for more protein and carbohydrate intake, and requires less fat intake. However, the drawback of the MAD is that can be difficult for patients on the MAD to comply with and to get enough fat to remain in ketosis.

WO 2015/034812 relates to a ketogenic diet and its use for treating the critically ill. It mentions that classic ketogenic diet has 3-4 g of fat per gram of protein and carbohydrate combined, but long term compliance being an issue. This remains unchanged but it focuses on the use of carbohydrates as the primary caloric source for the critically ill, since that gives rise to several attendant problems. In view thereof, the carbohydrate levels are lowered. The diet comprises a fat portion including DHA, EPA and MCTs that supplies 50-80% of the calories, a protein portion that supplies 10-35% of the calories and wherein any carbohydrate in the diet is limited to 0-10% of the calories. In example 1 there is provided an enteral composition with 100 g of each of fat and protein.

WO 2012/113415 describes compositions for malignant brain cancer and brain tumors. It refers to KetoCal® which is a nutritionally complete, commercially available 4:1 ketogenic formula. This ketogenic ratio is in line with comparative data provided in the examples and table 1 here below.

Mayumi Prins et al. "The collective therapeutic potential of cerebral ketone metabolism in traumatic brain injury" J. Lipid Research vol. 55 no. 12 (2014) p. 2450-2457 describes cerebral ketone metabolism in TBI. It mentions commercially available ketogenic formulas such as Bioserv F5848 (3:1), Bioserve F6666 (4:1) and Teklad 96355 (4:1).

Accordingly it is an object of the invention to provide for a dietetic and nutritional intervention that does not suffer from the above mentioned drawbacks of a ketogenic diet in subjects suffering from TBI and yet provides improved recovery from TBI.

SUMMARY OF THE INVENTION

The inventors have observed that enteral (preferably oral) administration of a nutritional composition comprising (a) a lipid, (b) a digestible carbohydrate fraction and (c) a protein fraction, wherein the lipid fraction comprises therapeutically effective amounts of (i) docosahexaenoic acid (22:6; DHA) and optionally eicosapentaenoic acid (20:5; EPA), and (ii) medium-chain triglycerides (MCT), preferably at least 2 wt % C8 and C10 MCT, based on weight of the fatty acids; and said nutritional composition (d) has a ketogenic weight ratio between 1.4:1 and 3:1, preferably between 1.8:1 and 2.7:1, more preferably between 1.8:1 and 2.5:1, for use in the treatment of traumatic brain injury (TBI). The nutritional composition is successful in improving recovery of a mammal subject (preferably a human person) suffering from traumatic brain injury. The composition according to the invention can therefore be used in the treatment of and recovery from traumatic brain injury (TBI), wherein the nutritional composition is administered enterally, preferably orally.

The nutritional composition preferably has a glycaemic index which is below 69, preferably below 65, the protein fraction preferably is present in a weight amount of at least 15 wt % of the composition, preferably at least 16-25 wt % of the composition, more preferably 17-21 wt % of the composition, and the composition preferably comprises at least fructo-oligosaccharides. In one embodiment, the composition more preferably also comprises cellulose, in which case the cellulose and fructo-oligosaccharides are preferably present in a weight ratio of 2:1 to 1:2.

In a preferred embodiment, the composition comprises therapeutically effective amounts of (i) docosahexaenoic acid (22:6; DHA) and eicosapentaenoic acid (20:5; EPA), preferably in an amount of 1-5 wt % of the sum of DHA and EPA, and (ii) medium-chain triglycerides (MCT), preferably at least 5 wt % of the sum of C8, C10 and C12 MCT, based on weight of the fatty acids; and said nutritional composition having a ketogenic weight ratio between 1.8:1 and 2.5:1, wherein said composition has a glycaemic index which is below 65, and wherein the protein fraction is preferably present in a weight amount of 17-21 wt % of the composition, and the composition preferably comprises at least fructo-oligosaccharides, more preferably cellulose and fructo-oligosaccharides, most preferably in a weight ratio of 2:1 to 1:2.

Reference is made to the TBI model in the experimental part. The effects of enteral (oral) intervention with the nutritional composition according to the invention ('Kone') on learning and spatial memory, (novel object) recognition and anxiety, and motor balance and alertness were assessed in a TBI mouse model. Intervention showed successful for each of these aspects which were found otherwise compromised in the context of TBI.

The invention further relates to a method for the transition to and/or the maintenance of a ketogenic metabolism comprising administering a nutritional composition comprising (a)-(i), (a)-(ii) and (b) as defined above, to a subject suffering from traumatic brain injury and/or symptoms related to traumatic brain injury.

FIGURES

The present invention will be discussed in more detail below, with reference to the attached figures, in which:

FIG. 1 depicts the time line of the experiments performed in experiment 1 wherein C57B16 mice were divided into 4 experimental groups 1) a control group undergoing craniotomy and exposed to the control diet (cranio control), 2) a group exposed to controlled cortical impact (CCI) model of TBI (TBI treatment) and receiving the control diet (CCI control), 3) a group that undergoes TBI treatment and receives FortasynConnect diet comprising DHA, EPA, UMP, choline, folic acid, selenium, phospholipids and vitamins B6, B12, C and E (CCI-FC) and 4) a group that undergoes TBI treatment and receives a modified ketogenic diet according to the invention (CCI-Kone).

Figure 2A:
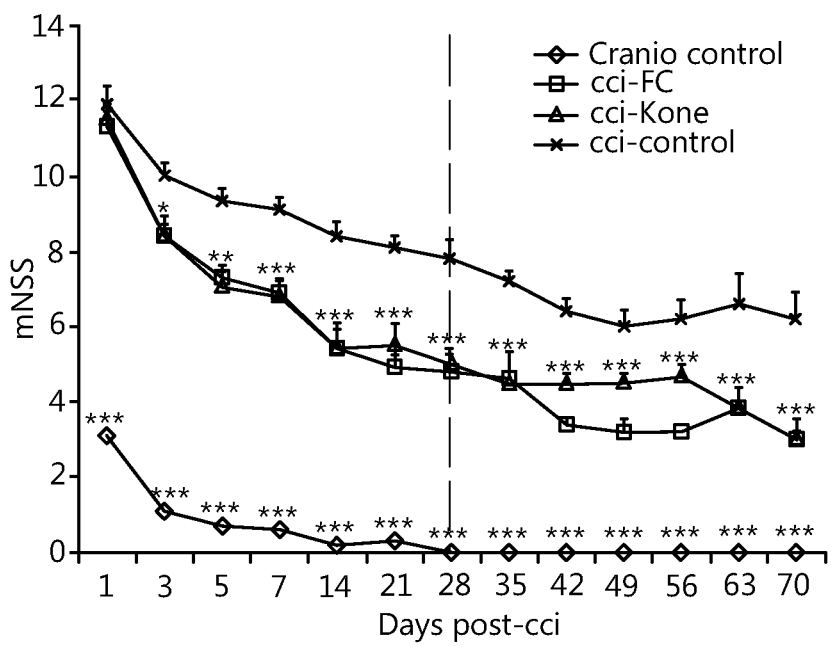
Figure 2B:
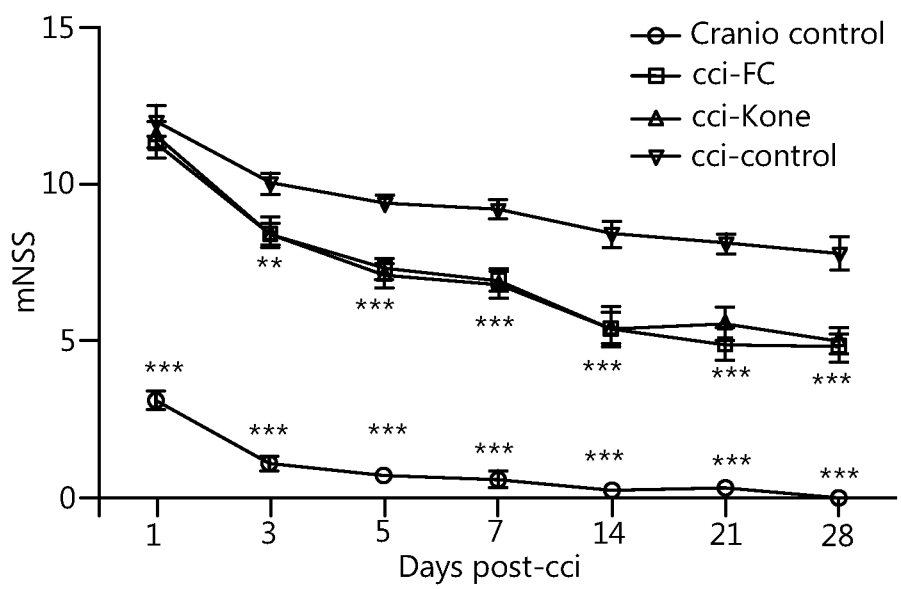

FIG. 2A shows the modified neurological severity score (mNSS) of the 4 different treatment groups of mice of experiment 1 over a period of 70 days post TBI treatment or control intervention. FIG. 2B shows the mNSS from day 1 to day 28 post TBI or control intervention in said 4 groups of animals. The neurobehavioural outcome assessed using the mNSS shows a significant improvement for CCI-FC and CCI-Kone treated animals relative to the CCI control group. Improvements as early as 3 days post-trauma are noted, lasting for the whole duration of the study. * $p<0.05$; $p<0.01$; *$p<0.001$ versus CCI-control animals.

Figure 3:
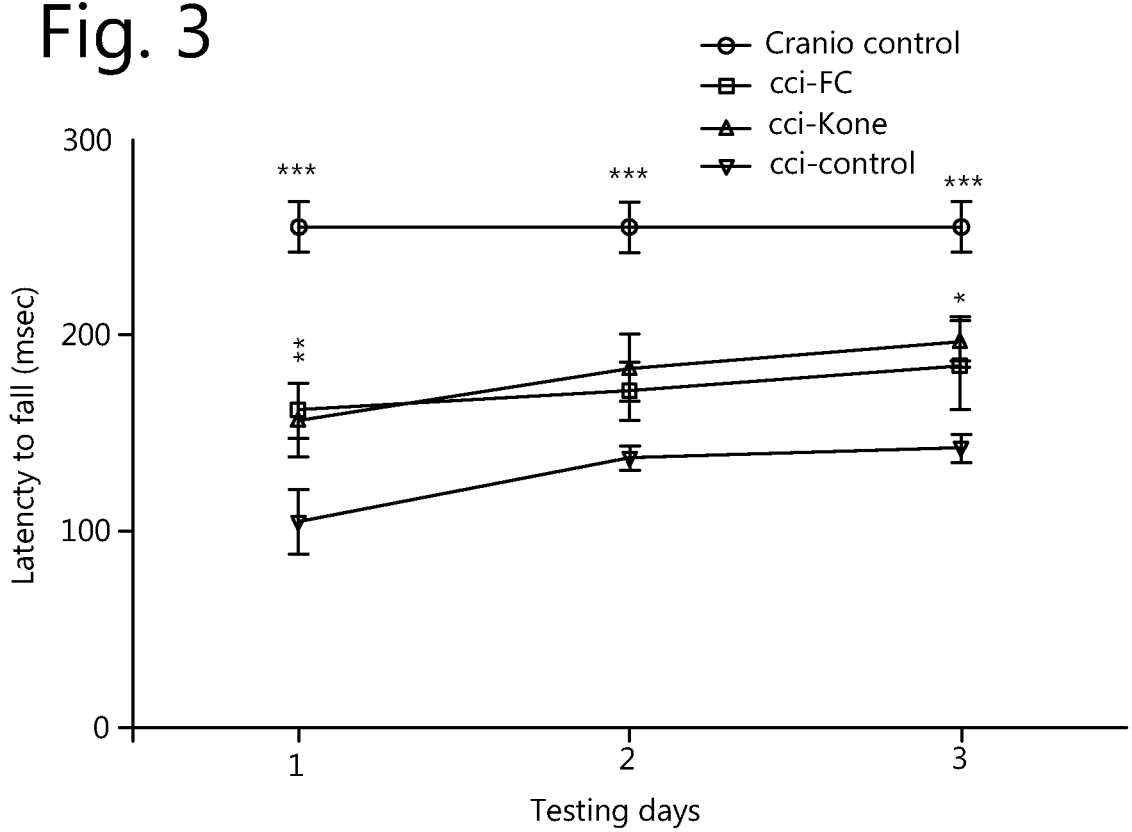

FIG. 3 shows the latency to fall in milliseconds (msec) from the Rotarod on 3 testing days in the 4 groups of animals. The CCI-FC and CCI-Kone treatment decreased the injury-induced impairment in the Rotarod test, which was carried out in the injured animals in the first 3 days post-injury. *$p<0.05$; ***$p<0.001$ vs. CCI-control animals.

Figure 4:
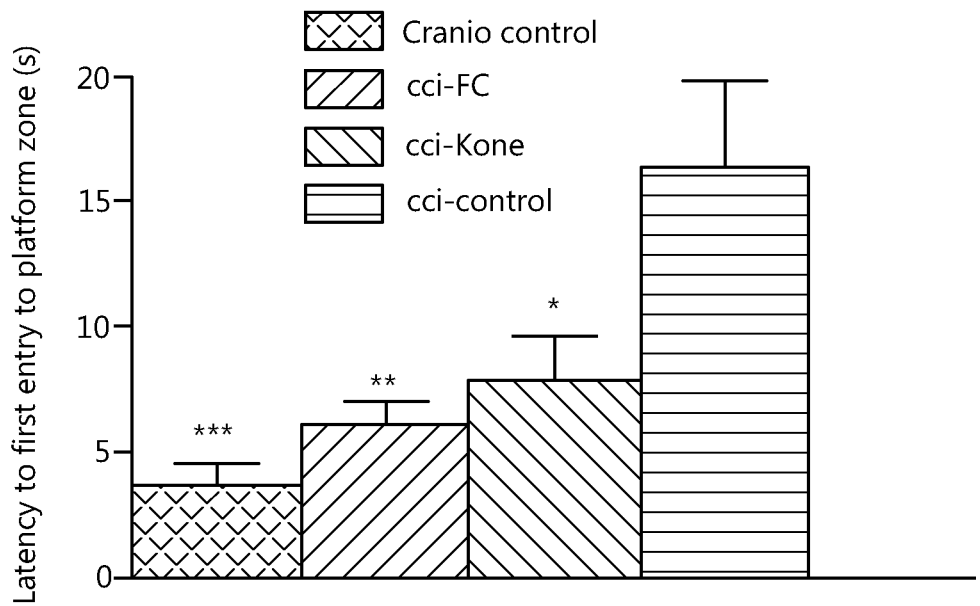

FIG. 4 shows the mean latency to first entry to the platform zone in seconds in the Morris Water Maze (MWM) in the 4 treatment groups. In the WMW test, the injury-induced deficit revealed in the probe trial was abolished by the Kone and FC-supplemented diets in the CCI-Kone and CCI-FC groups respectively.

Figure 5:
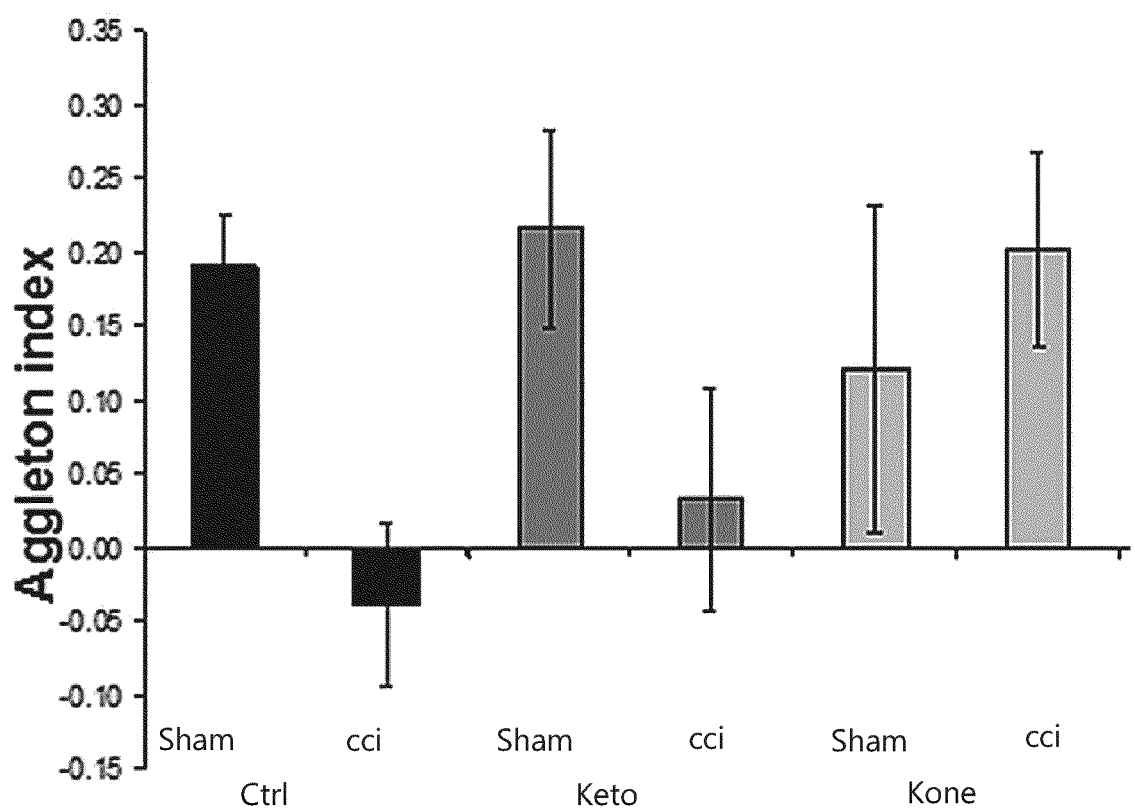

FIG. 5 shows the Novel Object Recognition Test results of experiment 2 which was performed with 6 different groups of C57B16 mice. The mice were first divided in craniotomy (sham) and mice that underwent TBI treatment (CCI) and after intervention allocated to the following dietary intervention groups receiving 1) the control diet (control), 2) ketogenic diet comprising 73 wt % lipids (keto) or 3) modified ketogenic diet according to the invention (Kone). Control treatment did not impair novel object recognition, whereas CCI treatment induced a major impairment in explorative behavior which was significantly reversed in the CCI group treated with Kone (CCI-Kone). The differences between groups was tested with One-way ANOVA *P<0.05.

Figure 6:
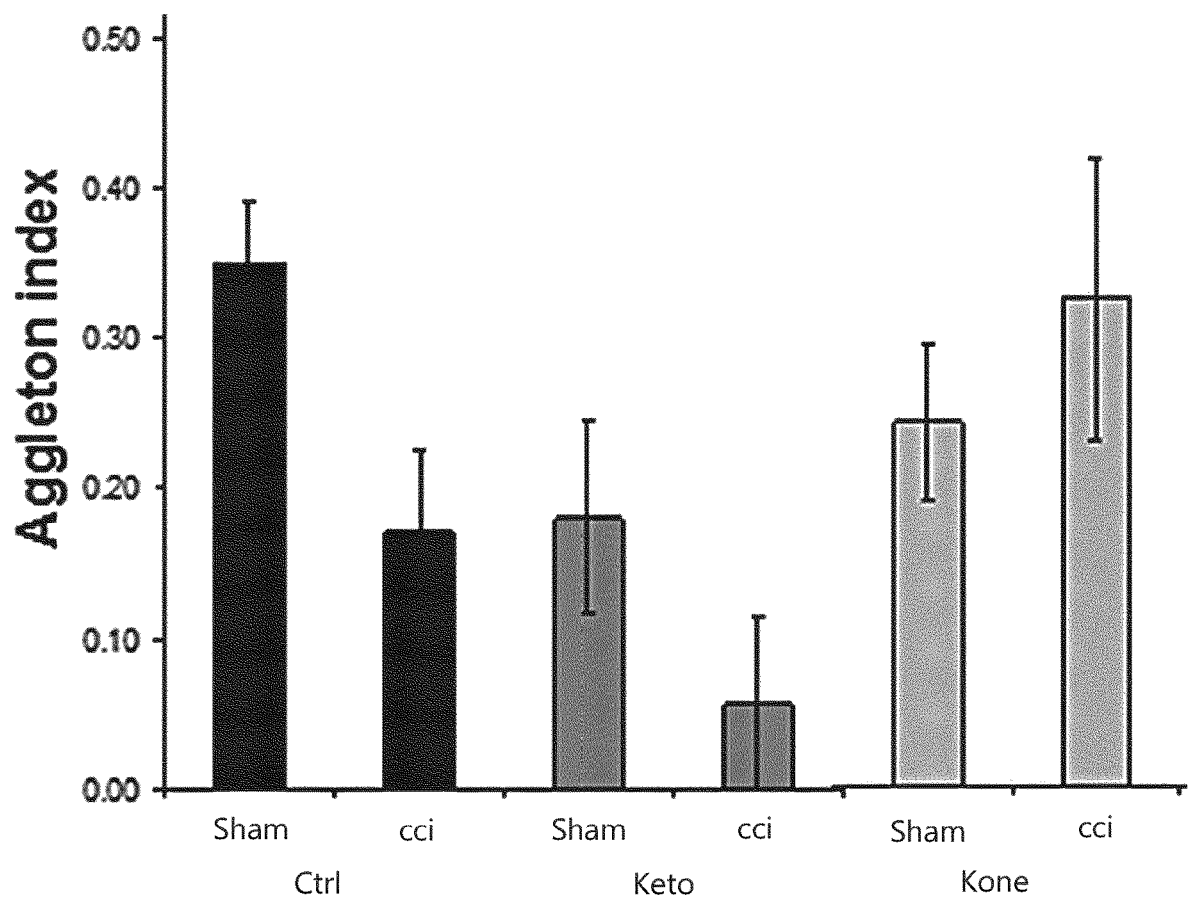

FIG. 6 shows for the animals of experiment 2 that CCI intervention leads to impairment in explorative behaviour and spatial recognition of the mice, an effect which is reversed upon treatment with Kone in the CCI-Kone group.

Figure 7:
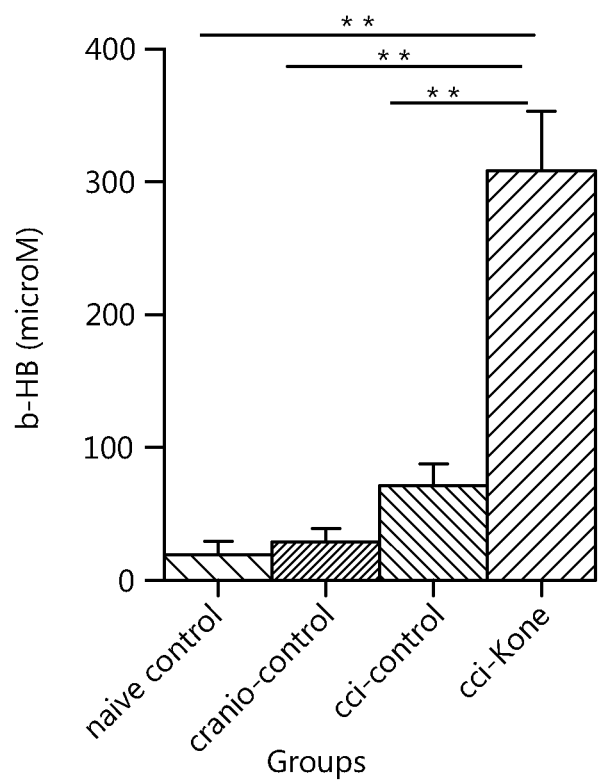

FIG. 7 plots the plasma levels of beta-hydroxybutyrate (b-HB) which show to be higher in the CCI-Kone group compared to the other groups (naieve control, cranio-control and CCI-control): ** p<0.01.

LIST OF PREFERRED EMBODIMENTS

1. An enteral nutritional composition comprising (a) a lipid fraction, (b) a digestible carbohydrate fraction and (c) a protein fraction, wherein the lipid fraction comprises therapeutically effective amounts of:
   (i) DHA and optionally EPA, and
   (ii) medium-chain triglycerides, preferably at least 2 wt % C8 and C10 medium-chain based on weight of the fatty acids;
   and wherein the composition has a ketogenic weight ratio between 1.4:1 and 3:1,
   for use in the treatment of traumatic brain injury (TBI).
2. The enteral nutritional composition for use according to embodiment 1, wherein the glycaemic index of the composition is below 69, preferably below 65.
3. The enteral nutritional composition for use according to embodiments 1 or 2, wherein the (c) protein fraction has a branched-chain amino acid content preferably comprising at least 10 wt % free leucine based on the weight of the protein fraction.
4. The enteral nutritional composition for use according to any of the preceding embodiments comprising less than 2 wt % ALA based on the weight of the fatty acids.
5. The enteral nutritional composition for use according to the preceding embodiments, wherein treatment of TBI involves enhancing recovery rate from TBI.
6. The enteral nutritional composition for use according to the preceding embodiments, wherein treatment of TBI involves enhancing sensorimotor recovery from TBI.
7. The enteral nutritional composition for use according to the preceding embodiments, wherein treatment of TBI involves enhancing cognitive recovery from TBI.
8. The enteral nutritional composition for use according to the preceding embodiments, wherein treatment of TBI involves improving spatial memory after TBI.
9. The enteral nutritional composition for use according to the preceding embodiments, wherein the composition is a tube feed.
10. Use of an enteral nutritional composition comprising (a) a lipid fraction, (b) a digestible carbohydrate fraction and (c) a protein fraction, wherein the lipid fraction comprises therapeutically effective amounts of (i) DHA and optionally EPA, and (ii) medium-chain triglycerides, preferably at least 2 wt % C8 and C10 medium-chain triglycerides based on weight of the fatty acids, and wherein the composition has a ketogenic weight ratio between 1.4:1 and 3.0:1, in the manufacture of a product for treating TBI.
11. A method for treating traumatic brain injury (TBI), comprising administering an enteral nutritional composition comprising (a) a lipid fraction, (b) a digestible carbohydrate fraction and (c) a protein fraction, wherein the lipid fraction comprises therapeutically effective amounts of (i) DHA and optionally EPA, and (ii) medium-chain triglycerides, preferably at least 2 wt % C8 and C10 medium-chain triglycerides based on weight of the fatty acids, and wherein the composition has a ketogenic weight ratio between 1.4:1 and 3.0:1.
12. An enteral nutritional composition comprising (a) a lipid fraction, (b) a digestible carbohydrate fraction and (c) a protein fraction, wherein the lipid fraction comprises:
   (i) DHA and optionally EPA, and
   (ii) medium-chain triglycerides, preferably at least 2 wt % C8 and C10 medium-chain triglycerides based on weight of the fatty acids, and wherein the composition (d) has a ketogenic weight ratio between 1.4:1 and 3.0:1.
13. The enteral nutritional composition according to embodiment 12, wherein the glycaemic index of the composition is below 69, preferably below 65.
14. The enteral nutritional composition according to embodiments 12 or 13, wherein the (c) protein fraction has a branched-chain amino acid content preferably comprising at least 10 wt % free leucine based on the weight of the protein fraction.
15. The enteral nutritional composition according to according to any of embodiments 12-14, comprising less than 2 wt % ALA based on the weight of the fatty acids.

DESCRIPTION OF EMBODIMENTS

The inventors found that a composition according to the invention is effective in the treatment of TBI and improves the recovery from TBI and neurobehavioural symptoms associated therewith.

The method and use of the invention comprises administering the composition as outlined below to a mammal subject in need thereof, preferably a human person in need thereof, suffering from TBI or suffering from cognitive and/or sensorimotor injury secondary to TBI.

In a preferred aspect the composition according to the invention is administered at least shortly after diagnosis of TBI, preferably starting within 2 hours after the diagnosis of TBI. In a preferred aspect the administration or use of the composition is prescribed for at least 5 days, more preferably at least 7 days, even more preferably at least 14, most preferably at least 1 month, particularly at least 3 months.

In one embodiment, the composition is used as sole nutrition. In a preferred embodiment the composition provides between 10% and 30% of the daily energy intake, more preferably between 15% and 25%.

In one preferred embodiment, the subject suffering from TBI or recovering from TBI has a ketostatus or ketosis status. In an aspect of the invention the composition may be used as part of a ketogenic diet.

In one aspect, the invention is directed to a composition as described here below, for use in the prevention and/or treatment of conditions characterized by impaired brain function resulting from TBI-induced brain dysfunction, i.e. in a subject suffering from or recovering from TBI.

In one aspect, the invention is directed at a composition as described here below, for use in the prevention and/or treatment of sensorimotor impairments and/or cognitive impairments in a subject suffering from the consequences of TBI or recovering from TBI.

Alternatively, the invention is directed at the use of a composition as described below in the manufacture of a composition for the treatment of TBI and cognitive and/or sensorimotor symptoms resulting from TBI.

In one aspect the invention involves an enteral nutritional composition comprising (a) a lipid fraction, (b) a digestible carbohydrate fraction and (c) a protein fraction, wherein the lipid fraction comprises therapeutically effective amounts of: (i) DHA and optionally EPA, and (ii) medium-chain triglycerides, preferably at least 2 wt % C8 and C10 medium-chain based on weight of the fatty acids; and wherein the composition has a ketogenic weight ratio between 1.4:1 and 3:1, for use in the treatment of traumatic brain injury (TBI). In one aspect, the invention involves a composition comprising therapeutically effective amounts of (i) docosahaenoic acid (22:6; DHA) and optionally eicosapentaenoic acid (20:5; EPA), and (ii) medium-chain triglycerides (MCT), preferably at least 2 wt % C8 and C10 MCT based on weight of the fatty acids, and (iii) LA and ALA preferably in a weight ratio in the range of 8:1 to 12:1; (b) a protein fraction comprising at least 10 wt % free leucine based on the weight of the protein fraction and (c) a digestible carbohydrate fraction comprising low glycemic index carbohydrates, preferably galactose and isomaltulose; and wherein (d) said nutritional composition has a ketogenic ratio between 1.4:1 and 3:1.

Throughout this application, the following terminology and abbreviations may be used:

Medium chain triglycerides (MCTs) are a type of fat found in a small number of foods, such as coconut oil and palm kernel oil. MCTs are defined to be linear or branched, preferably linear, saturated carboxylic acids having six (C6: 0), seven (C7:0), eight (C8:0), nine (C9:0), ten (C10:0), eleven (C11:0) or twelve (C12:0) carbon atoms.

A classical ketogenic diet comprises an amount of lipids (by weight), which is typically 4-fold the weight of the sum of proteins and digestible carbohydrates. In the context of the invention, the so-called ketogenic (weight) ratio is the weight ratio of the amount of lipid to the combined weight amounts of protein and digestible carbohydrates in the composition. The composition of the invention is preferably characterized by a ketogenic weight ratio between 1.4:1 and 3:1, more preferably between 1.6:1 and 2.9:1, more preferably between 1.8:1 and 2.7:1, more preferably 1.8:1 and 2.5:1, most preferably between 2:1 and 2.5:1. In a preferred embodiment a diet according to the invention is provided with a ketogenic weight ratio of about 2.3:1. Within the aforementioned (sub)ranges of ketogenic ratios of the invention, the composition according to the invention preferably comprises a lipid content that is at least twice the carbohydrate content by weight.

The glycemic index (GI) of a food is a ranking from 0-100 of the postprandial effect of a specific food on blood glucose levels. The standard for a score of 100 is pure glucose. On the scale of 1-100, scores of a food composition below 55 are generally considered low by those skilled in the art and scores between 59 and 56 moderate.

Traumatic brain injury refers to damage to the brain resulting from external mechanical force. TBI can result from falls, firearm wounds, sports accidents, construction accidents and vehicle accidents, among other causes. As it appears, traumatic brain injury is the most prevalent injury of soldiers in combat (e.g. amongst the US troops in Iraq and Afghanistan). Victims of TBI can suffer from a number of physical, cognitive, social, emotional and/or behavioural disorders following injury. The primary impact results in direct neural cell loss predominantly exhibiting necrotic death, which is then generally followed by a wave of secondary injury cascades including excitotoxicity, oxidative stress, mitochondrial dysfunction, blood-brain barrier disruption, and inflammation. According to the diagnostic criteria detailed in the "Diagnostic and Statistical Manual of Mental Disorders (DSM-5) TBI has one or more of the following characteristics: changes in levels of consciousness; memory disturbances; confusion associated with deficits in orientation; neurological signs, such as brain injury observable on neuroimaging, new onset or worsening of seizure disorder, visual field deficits and hemiparesis.

On the behavioural level, TBI survivors experience a wide range of deficits; sensorimotor impairment is a common consequence of this injury including elements of paresis, postural imbalance. gait disturbance, and early acute disruption of the startle reflex. These sensorimotor impairment following TBI can be assessed using the modified Neurological Severity Score (mNSS), Rotarod and gait analysis as further explained below.

TBI also often leads to deficits in cognitive domains, such as memory, attention and information-processing speed. Spatial memory after TBI can be assessed in mice using the Morris water maze (MWM), memory alterations w assessed thought visual object recognition memory using the novel object recognition test. Spatial memory and recognition can be assessed using the Y maze alternation. In addition TBI survivors frequently present with a delayed development of increased anxiety, agitation and also disinhibition in behaviour. Behavioural inhibition and anxiety are assessed using the elevated zero-maze in mice.

The modified Neurological Severity Score (mNSS) is a protocol used to evaluate motor ability, balance and alertness of experimental. Intervention with the composition of the invention resulted in improved motor ability, balance and alertness after TBI. In one aspect of the invention treatment of TBI includes treatment and/or improvement of sensorimotor impairment after TBI. Sensorimotor recovery is the ability to sense movements, touch and position of the body or a limb and generate adaptive, planned coordinated movements.

The Morris Water Maze (MWM) is a behavioural test used to assess learning and spatial memory of rodents that have to locate a submerged platform using distal cues. Learning and spatial memory were found to be compromised in case of TBI. In one aspect of the invention treatment with the composition according to the invention in the TBI model results in improved performance in the MWM. In another aspect of the invention, intervention with therapeutic levels of the composition of the invention resulted in improved learning and spatial memory in a subject suffering from TBI.

The Novel Object Recognition test is based on the innate tendency of rodents to explore new objects within their environment and relates to the assessment of recognition memory. Successful recognition was manifested by the preferential exploration of the novel object. While recognition memory was found disturbed in mice following TBI, intervention with the composition of the invention resulted in improved NOR test results and improved recognition. In one aspect of the invention, treatment with therapeutic levels of the composition according to the invention results in improvements in recognition memory in subjects suffering from TBI.

The Y maze Alternation is a behavioural test for measuring the willingness of rodents to explore new environments. Rodents typically prefer to investigate a new arm of the maze rather than returning to one that was previously visited. Intervention with the composition of the invention resulted in improved explorative behaviour of the mice. In one aspect of the invention, treatment with therapeutic levels of the composition according to the invention results in improved spatial memory and spatial recognition in subjects suffering from TBI.

The Catwalk test performed using a CatWalk system is a sensitive gait analysis tool which is capable of detecting subtle motor deficits in animals in an observer-independent manner. Intervention with the composition according to the invention resulted in significantly improvements in gait impairment after TBI.

The present invention provides for a method for treating traumatic brain injury in a mammal by administering a therapeutically effective amount of a nutritional composition to the mammal within a therapeutically effective time period subsequent to the injury so as to reduce secondary injury in a brain of the mammal and to treat the traumatic brain injury in said mammal.

In one aspect of the invention, the treatment involves improving the recovery rate from TBI.

In an embodiment of the invention the method for treating TBI improves neurological and brain function after TBI. In a further embodiment of the invention the present method, product, use or composition for use improves recovery from TBI.

In one embodiment, the treatment improves one or more of sensorimotor recovery after TBI, cognitive recovery after TBI, behavioural performance after TBI and spatial memory after TBI.

In one aspect of the invention, the treatment improves sensorimotor recovery after TBI.

In another aspect of the invention, the treatment improves cognitive recovery after TBI.

In another aspect of the invention, the treatment improves behavioural performance after TBI.

In a further aspect of the invention, the treatment improves spatial memory after TBI.

In a further embodiment of the invention the present method, product, use or composition for use provides for the generation of ketone bodies, in particular acetoacetate, beta-hydroxybutyrate and acetone, wherein the plasma levels of ketone bodies are sufficient to provide for the therapeutic effect on subjects suffering from TBI. In a preferred embodiment the plasma concentration of the sum of all ketone bodies will not exceed 5 mM. The plasma concentrations of beta-hydroxybutyrate are preferably higher than 200 µM, more preferably higher than 250 µM.

In one aspect of the invention the composition is intended as complete nutrition, in an embodiment as a tube-feed.

In one aspect of the invention the present method, product, use of composition for use is an enteral composition, preferably for oral administration. In one aspect the composition may be in liquid form, in the form of a drink.

In an embodiment of the invention the present method, product, use or composition for use provides for the supplementation of ketone bodies and their precursors without inducing ketosis. In one aspect of the invention the method, product, use or composition for use is as daily, twice daily or a three times per day nutritional supplement.

Further details of the, composition according to the invention are provided here below. Wherever reference is made to the composition according to the invention or just the composition, this equally applies to the combination and the product according to the invention, as well as for the use thereof in the composition for use according to the invention, the use according to the invention and the method according to the invention. Similarly, references to the method according to the invention equally apply to the composition for use and use according to the invention, and vice versa.

The product, composition or combination of the invention is typically an enteral composition, i.e. preferably intended for oral administration. It is preferably administered in liquid form. Preferably, the composition comprises water in which the further components are dissolved or suspended. In a preferred embodiment the enteral composition according to the invention is easy to administer by tube, i.e. it has a low viscosity and a low density, it is pH neutral, has a good shelf stability, and does not segregate, agglomerate or sediment. Preferably the enteral composition according to the invention provides for a complete nutritional composition.

In an embodiment of the invention (d) the ketogenic ratio of the product, composition or combination of the invention is between preferably characterized by a ketogenic ratio between 1.4:1 and 3:1, more preferably between 1.6:1 and 2.9:1, more preferably between 1.8:1 and 2.7:1, more preferably between 1.8:1 and 2.5:1, most preferably between 2:1 and 2.5:1. In a preferred embodiment a diet according to the invention is provided with a ketogenic weight ratio of about 2.3:1. Within the aforementioned (sub)ranges of ketogenic ratios of the invention, the composition according to the invention preferably comprises a lipid content that is at least twice the digestible carbohydrate content by weight. In an embodiment the method for treating TBI involves oral administration of a product, composition or combination comprising a lipid fraction to a mammal subject in need thereof.

Lipid Fraction

Suitable sources of lipids to provide for the lipid fraction (a) according to the invention are food-grade ingredients, for example those derived from eggs, milks, vegetables or plant material, marine organisms like fish or algae, natural- or mutated organisms or the lipids prepared by modification of the natural lipids, processed lipids from these sources such as extracts, isolates, interesterified lipids and the like, synthetic compounds or combinations thereof.

In one embodiment the lipid fraction preferably provides up to 85% of the total amount of calories of the composition, combination or product according to the invention, more preferably up to 80% of the total amount of calories, more preferably up to 75% of the calories, more preferably up to 70% of the calories, preferably up to 65% of the calories. In one embodiment the lipid fraction preferably provides between 55 and 85% of the calories, more preferably between 55 and 80% of the calories, more preferably between 55 and 75% of the calories, even more preferably between 55 and 70% of the calories. The remainder of the calories is typically provided by digestible carbohydrates and proteins. This is based on the assumption that lipid, carbohydrates and protein generate approximately 9, 4 and 4 kcal/g, respectively, the 3 together making up for all caloric contributions of the composition.

ω-3 LC-PUFAs

The method, product, composition or combination of the invention preferably comprises therapeutically effective amounts of (i) at least one omega-3 long-chain polyunsaturated fatty acid (LC-PUFA; having a chain length of 18 and more carbon atoms) selected from the group consisting of docosahexaenoic acid (22:6, n-3; DHA), and eicosapentaenoic acid (20:5n-3; EPA). Preferably the present composition, product or combination comprises at least DHA.

The LCPUFAs are preferably provided as triglycerides, diglycerides, monoglycerides, free fatty acids or their salts or esters, phospholipids, lysophospholipids, glycerol ethers, lipoproteins, ceramides, glycolipids or combinations thereof. Preferably, the present product, composition or combination comprises at least DHA in triglyceride form. Suitable ω-3 LCPUFA and/or DHA sources include tuna oil, (other) fish oils, DHA-rich alkyl esters, algae oil, egg yolk, or phospholipids enriched with ω-3 LCPUFA e.g. phosphatidylserine-DHA. Preferably, a product, composition or combination according to the invention comprises fish oil providing the omega-3 LCPUFA(s). Another particularly suitable source for the omega-3 LCPUFA(s) is algae oil.

In terms of the product, composition, combination or method, the proportion of ω-3 LCPUFA (at least DHA, preferably DHA and EPA) of the total fatty acids in the method, product or composition is preferably 1 to 40%, more preferably 1 to 30 wt %, more preferably 1 to 15 wt %, more preferably 1 to 10 wt %, even more preferably 1 to 6 wt %, most preferably 1 to 3 wt % of the total lipid fraction. In a preferred embodiment the amount of long chain polyunsaturated fatty acids, so having a carbon number of more than 20 is at least 2 g per 100 g fatty acids, preferably 3-50 g per 100 g fatty acids, more preferably 4-35 g per 100 g fatty acids, most preferably 5-20 g per 100 g fatty acids.

In terms of daily dosage, the present method preferably comprises the administration of 400-5000 mg DHA+EPA per day, more preferably 500-4500 mg DHA+EPA per day, even more preferably 1000-4000 mg DHA+EPA per day, most preferably 1500-3000 mg per day. DHA is preferably administered in an amount of 200-4500 mg per day, more preferably 500-4000 mg per day, most preferably 750-3250 mg per day. EPA is preferably administered in an amount of 200-4500 mg per day, more preferably 500-4000 mg per day, most preferably 750-3250 mg per day.

ALA

It is preferred that the alpha-linolenic acid [18:3n-3, ALA] content of the composition is maintained at low levels. While products used in the treatment of Alzheimer's disease mention 'normal' ALA levels of higher than 3 wt % of the total fatty acid fraction, i.e. about 5 wt %, it is discovered that the ALA concentration is preferably maintained at levels less than 2.0 wt %, more preferably below 1.5 wt %, particularly below 1.0 wt %, calculated on the weight of all fatty acids. It is preferred that the composition comprises at least 0.5 wt % ALA calculated on the weight of the fatty acids. In the animal studies set out in the examples, levels were about 1.5 g per 100 g fatty acids.

In one embodiment the linoleic acid [18:2n-6, LA] concentration is also significantly reduced to an amount of <15 g/100 g fatty acids and even less than 10 weight %. The LA concentrations are preferably at least 1 weight % of the fatty acids.

The LA:ALA weight ratio is preferably in the range of 4:1 to 15:1, more preferably 7:1 to 12:1, even more preferably 8:1 to 12:1, most preferably 8.5:1 to 10:1.

In one embodiment, the weight ratio ω3/ω-6 in the composition of the invention is preferably in the range of 0.3:1 to 7:1, preferably in the range of 1.4:1 to 5.9:1, more preferably in the range of 3:1 to 5.5:1, most preferably between 3:1 and 5:1, in particular less than 5:1. The amount of ω-6 LCPUFAs is preferably less than 50 weight %, preferably 5 to 40 weight %, more preferably 8 to 30 weight % of the fatty acids in the composition.

Medium Chain Triglycerides (MCTs)

It is preferred that the composition, combination or product according to the invention comprises (ii) MCTs. MCTs produce more ketones than regular fat (which consists of mostly LCTs), incorporating high amounts of MCTs into the diet allows patients to stay in ketosis while consuming relatively higher amounts of protein and carbohydrates. MCTs are converted in the liver to beta-hydroxybutyrate and acetoacetate and therefore readily available for ketolysis in the brain. In one embodiment, the composition contains at least 1.0 wt %, preferably at least 1.5 wt %, more preferably at least 2.0 wt % of fatty acids of less than 14 carbon atoms. In a preferred embodiment the MCT fraction comprises at least 2 wt %, more preferably at least 2.5 wt % of C8:0 (caprylic or octanoic acid) and C10:0 (capric or decanoic acid) MCTs based on the total amount of fatty acids, more preferably at least 3.0 wt %, more preferably at least 3.5 wt % even more preferably at least 4.0%. In a further preferred embodiment the MCT fraction comprises at least 5 wt % of C8 and C10 and C12 (lauric or dodecanoic acid) MCTs based on the amount of fatty acids, more preferably at least 5.5 wt %, more preferably at least 6 wt % and even more preferably at least 6.5 wt, most preferably 7 wt % based on the amount of fatty acids. The composition according to the invention preferably comprises 1 to 10 wt % MCTs, preferably the composition comprises between 5-10 wt % MCTs based on the weight of fatty acids. In one embodiment, the sum of the weight of medium chain fatty acids C6:0+C7:0+C8:0 over the sum of the weight of C9:0 and C10:0 is less than 2:1, more preferably less than 1.8:1, more preferably less than 1.6:1, even more preferably less than 1.4:1.

Saturated Fatty Acids

In an embodiment of the invention the amount of saturated fatty acids (SFA) having a carbon length of 10 to 24 is less than 50 g per 100 g fatty acids, preferably 5-45 g per 100 g fatty acids, more preferably 5 to 30 g per 100 g fatty acids, and most preferably 5-15 g per 100 g fatty acids. In a preferred embodiment the saturated fatty acid fraction is enriched for palmitic acid (C16:0) wherein 'enriched' is defined as forming more than 30 wt % of the SFA fraction. In a preferred embodiment the SFA fraction comprises at least 50 wt % palmitic acid based on the SFA fraction, more preferably at least 65%, even more preferably at least 70 wt % of the SFA fraction. In an embodiment of the invention the fatty acids of the SFA fraction form at least 40 wt % of the total lipid fraction, preferably at least 45 wt %, even more preferably at least 50 wt %. In a further embodiment the SFA fraction forms at least 20 wt %, more preferably at least 25 wt % of the nutritional composition. In one embodiment the amount of C16:0 and C18:0 fatty acids is between 50 and 85 wt % of the SFA fraction, preferably between 60 and 80 wt %, even more preferably between 70 and 75 wt %.

In an embodiment of the invention the amount of monounsaturated fatty acids (MUFA) is between 30 and 65 g per 100 g fatty acids. In a preferred embodiment, the lipid fraction comprises oleic acid. In other words, the MUFA fraction preferably comprises or even is oleic acid.

Phospholipids

The present composition preferably comprises at least one phospholipid in an amount of 0.01 to 1 gram per 100 ml, more preferably between 0.05 and 0.5 gram per 100 ml, most preferably 80 to 600 mg per 100 ml. In an embodiment, the composition comprises 0.01-10 wt %, preferably 0.1-8 wt % phospholipids, more preferably 1-6 wt % phospholipids, based on the total weight of lipids. The phospholipid fraction is preferably at least partly, more preferably completely, provided by lecithin, preferably soy lecithin. Thus, it is preferred that the composition comprises lecithin, preferably soy lecithin, in an amount to provide the above-mentioned phospholipid content.

Protein Fraction

The composition comprises a protein fraction (c). Protein includes all proteinaceous material, including intact and (partly) hydrolysed protein, peptides and amino acids. Any source of protein suitable to be used in a nutritional composition may comprised in the composition according to the invention. Preferred proteins sources include dairy proteins such as whey, casein, vegetables (beans, soy, lupin, amaranth, potato, seed, grains tubers, etc.), fish, krill, animals proteinaceous material, eggs and mushrooms. It is preferred that the protein fraction comprises protein from at least 2 sources.

In a preferred embodiment the protein fraction comprises casein and/or whey, preferably casein. In one embodiment the protein fraction comprises between 50 and 95 wt % casein and/or whey, preferably casein.

In one embodiment the protein fraction preferably provides up to 25% of the total amount of calories of the composition based on the sum of the proteins and amino acids in the protein fraction, more preferably up to 15% of the total amount of calories, more preferably up 11% of the calories, more preferably up to 10% of the calories, even more preferably up to 8% of the calories. In a preferred embodiment the protein fraction provide between 8 and 25% of the calories of the composition, more preferably between 9 and 15% of the calories, more preferably between 10 and 12% of the calories.

In a preferred embodiment, the protein faction is present in a weight amount of at least 15 wt % of the composition, preferably at least 16-25 wt % of the composition, more preferably 17-21 wt % of the composition.

In one embodiment the protein fraction comprises free branched chain amino acids valine, leucine and isoleucine. In a more preferred embodiment of the invention the protein fraction comprises the branched chain amino acid leucine in free form. The protein fraction preferably comprises at least 15 wt % of said branched chain amino acids, more preferably between 15 and 35 wt %, even more preferably between 16 and 30 wt %, particularly 17-25 wt %, based on the total protein content. These amino acids are preferably provided in free form. Preferably, the protein fraction comprises at least 10 g branched chain amino acids per 100 g protein fraction, preferably at least 15 g branched chain amino acids per 100 g protein fraction, preferably 15-35 g branched chain amino acids per 100 g protein fraction, more preferably at least 20 g branched chain amino acids per 100 g protein fraction, even more preferably at least 25 g branched chain amino acids per 100 g protein fraction. In an embodiment the protein fraction comprises up to 30 g branched chain amino acids per 100 g protein fraction. Preferably the branched chain amino acids are in free form, i.e. not part of a protein or peptide sequence. Preferably the branched chain amino acids comprise at least leucine in its free form. Per 100 g protein the amount of free leucine is typically between 5 and 15 g, even more preferably the amount of leucine is between 10 and 15 g in free form. In one embodiment the total amount of L-leucine provided by the protein fraction preferably amounts to at least 7 wt %, preferably at least 8 wt %, more preferably 9-20 wt % based on total protein fraction. In the context of the invention, the terms 'leucine' and 'L-leucine' are used interchangeably. In an embodiment the amount of free leucine to the total amount of leucine in the protein is fraction is between 1:15 and 1:1, more preferably between 1:10 and 1:2.

In an embodiment of the invention it is preferred that the protein fraction comprises a relatively large content of ketogenic amino acids such as lysine and leucine that can be converted into ketone bodies, and a relatively low content of glucogenic amino acids that can be metabolically converted into glucose through gluconeogenesis, such as glutamine, glutamate, alanine, glycine and serine. In one embodiment, the weight ratio of [lysine+leucine] to [glutamate+glutamine+alanine+glycine+serine] is preferably at least 0.5, such as in the range of 0.5 to 10. It is believed that a high ratio of ketogenic amino acids to the sum of glucogenic amino acids aids in the maintenance of the ketogenic character of the composition, combination or product according to the invention.

Carbohydrate Fraction

The composition according to the invention comprises a carbohydrate fraction (b), preferably the present composition comprises a digestible carbohydrates. The composition may also comprise non-digestible carbohydrates or dietary fiber or nutritional fiber. In a preferred embodiment, the carbohydrate fraction comprises (cellulose and) fructo-oligosaccharides, in case both are present preferably in a weight ratio of 2:1 to 1:2.

Digestible Carbohydrates

Typically, any digestible carbohydrates that are known in the art to be suitable for use in nutritional compositions may be used. Preferably, the digestible carbohydrate is selected from digestible polysaccharides (e.g. starch, maltodextrin), digestible monosaccharides (e.g. glucose, fructose, galactose), and digestible disaccharides (e.g. lactose, sucrose, isomaltulose). Preferably, the composition comprises digestible carbohydrates rich in one or more of non-glucose and non-fructose saccharides such as mannose, galactose, xylulose, xylose, glucosamine and sialic acid. In a preferred embodiment, the composition according to the invention comprises one or more low glycemic index carbohydrates selected from palatinose, trehalose, lactose, galactose and isomaltulose. In a preferred embodiment the composition, combination or product according to the invention comprises galactose and isomaltulose. Low GI carbohydrates are carbohydrates having a GI of 55 or less.

In a preferred embodiment the carbohydrate fraction of the composition comprises between about 70 and 100 wt % low glycemic index carbohydrates, more preferably between 80 and 95 wt %, more preferably between 85 and 95 wt %.

The amount of galactose is preferably between about 25 wt % and 45 wt % of the carbohydrate fraction, more preferably between about 30 wt % and 40 wt % of the carbohydrate fraction and in an even more preferred embodiment between about 35 wt % and 40 wt % of the carbohydrate fraction. The amount of isomaltulose is in one embodiment preferably between about 55 wt % and 75 wt % of the carbohydrate fraction.

The amount of glucose or rapidly digestible glucose polymers is preferably below 10 wt % of the carbohydrate fraction, more preferably below 5 wt % of the carbohydrate fraction, even more preferably below 1 wt % of the carbohydrate fraction.

In one embodiment the digestible carbohydrate fraction preferably provides up to 5% of the total amount of calories of the composition, more preferably up to 8% of the total amount of calories, more preferably up 10% of the calories, more preferably up to 15% of the calories, even more preferably up to 20% of the calories. The digestible carbohydrate fraction of the composition provides at least 1% of the calories of the composition, more preferably at least 2%.

In one embodiment the glycemic index (GI) of the composition is below 70, preferably below 65, preferably below 60, more preferably below 55. In a preferred aspect the glycemic index is between 65 and 55, wherein the glycemic index is based on glucose as reference value set at 100.

Vitamins

In one embodiment, the present combination comprises at least one B complex vitamin. The vitamin B is selected from the group of vitamin B1 (thiamine), vitamin B2 (riboflavin), vitamin B3 (niacin or niacinamide), vitamin B5 (pantothenic acid), vitamin B6 (pyridoxine, pyridoxal, or pyridoxamine, or pyridoxine hydrochloride), vitamin B7 (biotin), vitamin B9 (folic acid or folate), and vitamin B12 (various cobalamins). Functional equivalents are encompassed within these terms.

In one embodiment, at least one vitamin B is selected from the group of vitamin B6, vitamin B12 and vitamin B9. Preferably the present composition comprises at least two selected from the group consisting of vitamin B6, vitamin B12 and vitamin B9. In particular, good results have been achieved with a combination of B vitamins comprising or consisting of vitamin B6, vitamin B12 and vitamin B9. The vitamin B, preferably vitamin B6, B9 and/or B12, is to be administered in a therapeutically effective dose.

If present in the nutritional composition or medicament, the vitamin B6 is preferably present in an amount to provide a daily dosage in the range of 0.1 to 100 mg, in particular in the range of 0.5 to 25 mg, more in particular in the range of 0.5 to 5 mg. The present composition preferably comprises 0.1-100 mg vitamin B6 per 100 g (liquid) product, more preferably 0.5-5 mg vitamin B6 per 100 g (liquid) product, more preferably 0.5-5 mg vitamin B6 per 100 g (liquid) product.

If present in the nutritional composition or medicament, the vitamin B12 is preferably present in an amount to provide a daily dosage in the range of 0.5 to 100 μg, in particular in the range of 1 to 10 μg, more in particular in the range of 1.5 to 5 μg. The present composition preferably comprises 0.5-100 μg vitamin B12 per 100 g (liquid) product, more preferably 1-10 μg vitamin B12 per 100 g (liquid) product, more preferably 1.5-5 μg vitamin B12 per 100 g (liquid) product. The term 'vitamin B12' incorporates all cobalamin equivalents known in the art.

If present in the nutritional composition or medicament, the vitamin B9 (folic acid) is preferably present in an amount to provide a daily dosage in the range of 50 to 5000 μg, in particular in the range of 100 to 1000 μg, more in particular in the range of 200 to 800 μg. The present composition preferably comprises 50-5000 μg folic acid per 100 g (liquid) product, more preferably 100-1000 μg folic acid per 100 g (liquid) product, more preferably 200-800 μg folic acid per 100 g (liquid) product. Folates include folic acid, folinic acid, methylated, methenylated and formylated forms of folates, their salts or esters, as well as their derivatives with one or more glutamic acid, and all in either reduced or oxidized form.

The composition of the invention preferably comprises, if at all, less than 100 mg, more preferably less than 50 mg, more preferably less than 25 mg uridine equivalents, calculated as uridine, per 100 g (liquid) product. Alternatively, the method of use of the invention preferably involves less than 50 mg, more preferably less than 25 mg uridine equivalents, calculated as uridine, per daily dose. In one embodiment, there are no detectable amounts of uridine and UMP.

The composition of the invention preferably comprises, if at all, less than 50 mg, more preferably less than 25 mg choline equivalents selected from choline, a choline salt and/or choline ester, calculated as choline, per 100 g (liquid) product.

In one embodiment of the invention a composition is envisioned not comprising uridine, uridine monophosphate (UMP) and choline.

In one embodiment, the composition of the invention does not comprise vitamins B6, B9 and B12, vitamins C and E, and selenium beyond FSMP guidelines.

In one embodiment the composition, combination or product according to the invention comprises per 100 gram product 5-9 g protein, 0.8 to 4 g nutritional fiber, 1.2-1.8 g digestible carbohydrates having a glycemic index value of less than 70, 15-24 g lipids comprising 3-20 wt % marine oils, 10-30 wt % MCT oils and the remainder of the lipid fraction formed from vegetable oils, wherein the ratio of lipids to the sum of proteins and digestible carbohydrates is 1.4-3:1. In one aspect said product is suitable for use in a subject suffering from TBI, wherein the subject is 6 years or older.

In one embodiment the product of composition comprises per 100 ml 1.3-1.9 g protein wherein the protein fraction comprises 10-15 g leucine per 100 g protein, 0.6-1.0 g digestible carbohydrates having a glycemic index value below 65, 5-7 g lipids wherein the lipid fraction comprises 5-50 wt % marine oil, 4-30 wt % MCT oil and vegetable oils, 0.4 to 4 g nutritional fiber, 0.3-0.5 g minerals, trace elements and vitamins, wherein the weight ratio of lipids to the sum of protein and digestible carbohydrates is 1.4:1-3:1. In one aspect, said composition or product is suitable for use in subject suffering from TBI, wherein said subject is below 6 years of age.

The compositions as described above can be used as a nutritional therapy, nutritional support, as a medical food, as a food for special medical purposes or as a nutritional supplement. Such product can be consumed at one, two or three servings per day during recovery and/or rehabilitation from traumatic brain injury. A typical serving size is of 125 mL. The compositions as described above can alternatively be used as complete nutrition as a medical food, as a food for special medical purposes or as tube feed.

EXAMPLES

For a more complete understanding of the present disclosure, reference is now made to the following examples taken in conjunction with the accompanying drawings.

Example 1—Exploration of the Neuroprotective Effects in a Mouse Model of Traumatic Brain Injury The effects of the composition comprising a lipid fraction comprising the modified ketogenic diet according to the invention as set out in table 1 was assessed in an experimental model of traumatic brain injury. Adult 10-12 week-old male C57BL/6 mice, weighing 22-27 g (Charles River Laboratories, Harlow, UK), were used. Mice were housed in groups of four in standard cages provided with enrichment objects, in a 12 h light/dark cycle, and given diet and water ad libitum. Food intake and body weight were monitored daily. All animal procedures were approved by the Animal Welfare and Ethical Review Body, at Queen Mary University of London and the UK Home Office, in accordance with the EU Directive 2010/63/EU.

A controlled cortical impact (CCI) TBI model was used in this study. Briefly, after a 1-week acclimatisation period, mice were anaesthetized using a mixture of ketamine (50 mg/Kg) and medetomidine (0.5 mg/Kg) in sterile saline, administered intraperitoneally (i.p.). Mice were placed in a stereotaxic frame and a midline longitudinal incision was performed to expose the skull. A right lateral craniotomy was carried out using a pneumatic drill, 2.0 mm behind bregma and 2.5 mm lateral to the midline. CCI injury was induced using the following settings: a 3 mm impactor tip with a speed of 3 m/s, a depth of 2.2 mm and a dwell time of 100 ms, applied using the PCI3000 Precision Cortical Impactor™ (Hatteras Instruments, Inc., US). A control group underwent craniotomy only (cranio control). After injury, the skull flap was placed back and the skin was sutured. Mice were allowed to recover in an incubator (37° C.) until they were fully awake and active. Buprenorphine (0.05 mg/kg) administered subcutaneously (s.c.) was used pre-operatively for pre-emptive analgesia and post-operatively every 12 h for 3 days post-TBI.

Following the injury, mice were randomized into three TBI groups and fed daily with a fresh control diet ('CCI-Control'; n=10), with a Fortasyn® Connect (FC) multi-nutrient combination diet ('CCI-FC'; n=10) or a modified Ketogenic multi-nutrient diet (CCI-Kone, n=11) for 70 days. Table 1 sets out the ingredients and fatty acid profiles of the control, FC and modified ketogenic (Kone) diet. The craniotomy group were daily fed with control diet (Craniotomy only; n=10). The diets were formulated by Nutricia Research, Nutricia Advanced Medical Nutrition (Utrecht, The Netherlands) and manufactured and pelleted by Ssniff (Soest, Germany). Diets were stored at −20° C. until use, to prevent lipid oxidation, and fresh diet was given to the animals daily. Diet stability under these conditions has been previously confirmed (Cansev et al., 2015). No significant differences were observed in the mean daily food intake and body weight gain (between groups, throughout the experiment).

TABLE 1A

Nutritional composition of the control, FC and modified ketogenic diet according to the invention (Kone) in grams per 100 g diet.

| | Control | FC | Kone |
|---|---|---|---|
| Cornstarch, pre-gelatinized | 45.59 | 30.85 | |
| Sucrose | 10 | 10 | |
| Maltodextrin, 10 DE | 15.5 | 15.5 | |
| Galactose | | | 1.5 |
| Isomaltulose | | | 2.72 |
| sum digestible carbohydrates | 71.09 | 56.35 | 4.22 |
| Caseine | 14 | 14 | 18.7 |
| Leucine | | | 1.9 |
| sum proteins + amino acids | 14 | 14 | 20.6 |
| Soy oil | 1.9 | | |
| Coconut oil | 0.9 | 0.1 | 4.4 |
| Corn oil | 2.2 | 0.1 | |
| Palm oil | | | 39.9 |
| DHA25 oil | | 4.5 | 5.7 |
| Rapeseed oil | | | 5.7 |
| MCT oil | | | 1.3 |
| Refined fish oil (EPA) | | 0.3 | |
| sum lipids | 5 | 5 | 57 |
| Cellulose powder | 5 | 5 | 5 |
| Fibers (FOS) | | | 5 |

TABLE 1A-continued

Nutritional composition of the control, FC and modified ketogenic diet according to the invention (Kone) in grams per 100 g diet.

| | Control | FC | Kone |
|---|---|---|---|
| Mineral & trace element premix (AIN-93M-MX) | 3.5 | 3.5 | 5.83 |
| Vitamin mix (AIN-93-VX) | 1 | 1 | 1.67 |
| L-cystine | 0.18 | 0.18 | 0.3 |
| Choline chloride (50%, 0.434 g/g) | 0.23 | 1.38 | 0.38 |
| Tert-butylhydroquinone | 0.0008 | 0.0008 | 0.0013 |
| Soy lecithin | | 1.1321 | |
| UMP disodium (24% H2O) | | 1.5 | |
| Ascorbic acid (100% pure) | | 0.24 | |
| Vitamin E (tocopherol acatate, 50%) | | 0.705 | |
| Vitamin B6 (pyridoxin hydrochloride, 82%) | | 0.0053 | |
| Folic acid (100%) | | 0.001 | |
| Vitamin B12 (cyanocobalamin 0.1%) | | 0.065 | |
| Na selenite•5H20 | | 0.0005 | |
| Ketogenic weight ratio | 0.06:1 | 0.07:1 | 2.3:1 |
| Total (g) | 100 | 100 | 100 |
| Energy (kcal/100 g diet) | 377 | 358.7 | 625.6 |

TABLE 1B

Fatty acid profiles of the control, FC and modified ketogenic diet according to the invention (Kone) in weight percentages based on the total amount of fatty acids.

| | Control | FC | Kone |
|---|---|---|---|
| C-6:0 | 0.09 | 0.02 | 0.05 |
| C-8:0 | 1.35 | 0.15 | 1.66 |
| C-10:0 | 1.08 | 0.12 | 1.29 |
| C-12:0 | 8.28 | 0.97 | 3.81 |
| C-14:0 | 3.24 | 4.00 | 2.43 |
| C-15:0 | 0 | 0.73 | 0 |
| C-16:0 | 10.32 | 16.67 | 33.34 |
| C-16:ω7 | 0.09 | 5.26 | 0.6 |
| C-17:0 | 0 | 0.88 | 0.12 |
| C-18:0 | 2.85 | 4.65 | 4.22 |
| C-18:1 ω9 | 21.81 | 13.75 | 35.64 |
| C-18:2 ω6 | 45.71 | 3.32 | 9.33 |
| C-18:3 ω3 | 2.25 | 0.80 | 0.97 |
| C-18:3 ω6 | 0 | 0.13 | 0.02 |
| C-18:4 ω3 | 0 | 0.02 | 0.1 |
| C-20:0 | 0.41 | 0.38 | 0.34 |
| C-20:1 ω9 | 0.21 | 2.02 | 0.14 |
| C-20:2 ω6 | 0 | 0.72 | 0 |
| C-20:3 ω6 | 0 | 0.17 | 0 |
| C-20:4 ω6 | 0 | 1.93 | 0.19 |
| C-20:5 ω3 | 0 | 9.07 | 0.6 |
| C-22:0 | 0.19 | 0.24 | 0.04 |
| C-22:1 ω9 | 0 | 0.26 | 0.05 |
| C-22:4 ω6 | 0 | 0.35 | 0 |
| C-22:5 ω3 | 0 | 1.56 | 0.12 |
| C-22:6 ω3 | 0 | 23.42 | 2.64 |
| C-24:0 | 0 | 0.17 | 0 |
| C-24:1 ω9 | 0 | 0.29 | 0 |
| Total FA | 100 | 100 | 100 |
| SAT.FA | 27.81 | 28.97 | 47.30 |
| MUFA | 22.11 | 21.59 | 36.43 |
| PUFA | 47.96 | 43.51 | 13.98 |
| Other FA | 2.12 | 5.93 | 2.29 |
| MCT | 10.80 | 6.81 | 6.81 |

Behaviour Testing

After the surgical intervention behavioural performance of the animals was followed over time. The protocol setting out the battery of behavioural tests is presented schematically in FIG. 1. Briefly for all animals the neurological severity score using 10 individual tests (table 2) was tested from day 1 to day 70 post intervention to evaluate motor ability, balance and alertness. All animals were trained on the Rotarod for 3 consecutive days prior to surgical intervention followed by assessment of Rotarod performance on days 1, 2 and 3 post intervention for the evaluation of motor coordination, motor-planning and balance. Catwalk performance was used for assessing the gait on days 1 and 2 after intervention. Animals were trained in a Morris Water Maze to assess memory deficits associated with spatial learning on days 13-17 after the intervention and on day 18 probe trial was performed wherein the time is measured for a mouse to find back a quadrant in the water maze where previously a platform was present.

TABLE 2

Neurologic Severity score tests and their corresponding functional assessments.

| Test | Functional Assessment |
|---|---|
| Exit circle | Ability and initiative to exit a circle of approximately 30 cm diameter (time limit: 2 min) |
| Para/Hemiparesis | Paresis/Spasticity of upper and/or lower limb of the contralateral side |
| Straight walk | Alertness, Initiative, and motor ability to walk straight |
| Seeking behaviour | Physiological behaviour as a sign of "interest" in the environment |
| Startle reflex | Innate reflex; the mouse will jump in response to a loud hand clap |
| Beam balancing (rectangular or triangular) | Ability to balance on a beam of 5 mm width with 4 paws for at least 10 seconds |
| Round stick balancing | Ability to balance on a round stick of 5 mm diameter with 4 paws for at least 10 seconds |
| Beam walk: 3 cm | Ability to cross a 30 cm long beam of 3 cm width with normal gait |
| Beam walk: 2 cm | Same task, increased difficulty on a 2 cm wide beam |
| Beam walk: 1 cm | Same task, increased difficulty on a 1 cm wide beam |

All the groups of animals showed a decrease in TBI-induced impairment, assessed with the integrated mNSS score, over 70 days after trauma, but a significant improvement was observed in CCI-Kone and CCI-FC-treated animals as early as the 3rd day post-trauma, compared to the CCI-control diet group. The significant difference in neurological score between the CCI-control diet and CCI-Kone and CCI-FC groups was maintained until the end of the study (FIG. 2A). The craniotomy control animals only showed a transient neurological impairment, which was resolved after the first week. In FIG. 2B the follow-up of the same animals in the first 28 days post intervention is shown. It is apparent therefrom that CCI-FC and CCI-Kone treated animals both have a significantly improved neurological score compared to the CCI-control treated animals.  $p<0.01$ and * $p<0.001$ versus CCI-control.

The Rotarod test carried out in the first 3 days post-injury (dpi) revealed better preservation of performance in both CCI-Kone and CCI-FC-treated injured animals (FIG. 3). The average latency time to fall off the Rotarod in msec was significantly higher in the CCI-Kone and CCI-FC animals, compared to the animals in the CCI-control group. The craniotomy-control group showed minimal coordination and balance impairment compared to CCI-groups.  $p<0.01$ and * $p<0.001$ versus CCI-control.

Spatial memory after TBI was assessed using the Morris water maze (MWM), a test extensively used in the study of TBI to detect impairments in hippocampal-dependent spatial learning and memory. CCI led to a disruption of the acquisition of this task as visualised in the CCI-control group having a significantly higher latency to first entry to the platform zone compared to both the CCI-FC and CCI-Kone treated animals. As illustrated in FIG. 4, the probe trial revealed a major impairment following CCI, which was totally reversed by treatment with the FC- or Kone supplemented diet. * $p<0.05$,  $p<0.01$ and * $p<0.001$ versus CCI-control.

Example 2—Comparison with Classical Ketogenic Diet in the Treatment of TBI

In a similar set-up as described above for example 1 3 groups of 20 mice were randomized into three dietary intervention groups to receive fresh control diet (ctrl n=20), a control ketogenic diet (keto, table 3 provides characteristics of the control ketogenic diet, Ketocal 4:1 unflavoured, Nutricia N.V. The Netherlands) or a modified ketogenic multi-nutrient diet according to the invention (Kone). Each group of 20 mice was divided in a group (n=10) that underwent craniotomy (sham) and a group that underwent TBI intervention (CCI). Following surgery mice were fed their allocated diet ad libitum for 70 days.

TABLE 3

Nutritional characteristics of the classic ketogenic diet used in experiment 2 in grams per 100 g diet.

| | g/100 g diet control ketogenic diet |
|---|---|
| Sum carbohydrates | 3.00 |
| Casein (>85% protein) | 15.25 |
| sum proteins + amino acids | 15.25 |
| Fibers | 0.0 |
| Sum fats | 73 |
| Total (g) | 91.3 |
| Energy (kcal/100 g diet | 730 |
| Ketogenic ratio | 4:1 |

At 22 to 25 days post intervention animals were trained in the Novel Object Recognition test wherein an empty opaque box used as open file and familiarized with 2 identical objects positioned in that field. Assessment of this natural tendency enables a determination of whether an animal is able to discriminate between a familiar object and a novel one. During the acquisition phases, two identical objects (A and B) were placed in a symmetric position within the arena for 5 min. These objects were suitably heavy and high to guarantee that mice could neither move nor climb over them. Twenty-four hours following this acquisition phase of training, one of the objects (either A or B, randomly) was substituted with a novel one (C), and the animal's exploratory behavior was again evaluated over 5 min. Following each session, all objects were meticulously cleaned with 70% ethanol to preclude odor recognition. Exploration of an object was defined as rearing on the object or sniffing it at a distance of less than 2 cm, and/or touching it with the nose. Successful recognition was manifested by the preferential exploration of the novel object. The time spent with either a novel and a familiar object was measured to evaluate recognition memory wherein an absence in any difference in the exploration of the two objects can be interpreted as a memory deficit. Results of this Novel Object Recognition test are shown in FIG. 5. Results are expressed as the Aggleton index: [time near the new object−time near the familiar object]/[time near the new object+time near the familiar object], a measure of the relative time spent investigating the novel object. As illustrated in FIG. 5 control treatment (sham) did not impair novel object recognition (control mice spent the highest proportion of time with the novel object), whereas CCI treatment induced a major impairment which was partly reversed in the CCI-Keto group and totally reversed in the CCI-Kone group exposed to the Kone diet.

At 45 days post intervention the Y-Maze alternation was used to assess exploratory behaviour and spatial memory. The maze consisted of three identical arms separated by a 120° angle and built from black Plexiglas. Each arm was 8×30×15 cm and differed solely by the presence of specific visual cues (a triangle, a square, or a circle). One arm was randomly selected as the "start" arm. On the first trial, lasting for 5 min, each mouse was placed into the start arm and one of the two remaining arms was randomly blocked to limit access. By contrast, during the second trial, lasting for 2 min, all arms of the maze were open. These two trials were separated by a 2 min interval, during which the mouse was returned to its home cage. The time spent in each of the arms was measured during the two trial periods. Between trials, the maze was thoroughly cleansed using a 70% ethanol solution, and was then dried. A discrimination preference index was calculated according to Aggleton: [time in the new arm−time in the familiar arm]/[time in the new arm+time in the familiar arm]. As illustrated in FIG. 6, control craniotomy treatment (sham) did not impair explorative behaviour, whereas CCI-treatment induced a major impairment in explorative behaviour in the Y-maze which was not reversed in the CCI-Keto group, yet totally reversed in the CCI-Kone group exposed to the K-one diet. Treatment with therapeutic levels of the composition according to the invention results in improved spatial recognition and spatial memory following TBI.

FIG. 7 shows plasma levels of beta-hydroxybutyrate (h-BH) for the different groups. For the assessment of beta-hydroxybutyrate (b-HB) levels in mouse plasma samples, the colorimetric beta-Hydroxybutyrate Assay Kit (Sigma-Aldrich) was used in accordance to manufacturer's instructions. Briefly, plasma samples were centrifugated to remove any large debris, but the samples were not deproteinated. Per sample, 25 µl of plasma was transferred to a 96-wells plate. A mastermix was then prepared containing assay buffer with the 3-hydroxybutyrate dehydrogenase and enzyme substrate. For background correction, a separate mastermix was prepared without the b-HB enzyme mixture. These mastermixes were then added to the 96-wells plate containing the plasma and incubated at room temperature for 30 minutes. Subsequently, b-HB levels were determined by measuring the OD at 450 nm using the FlexStation III multimode plate reader. For each experiment a b-HB standard curve was measured. B-HB content were determined by subtracting the background OD from the sample OD measurements, using the standard curve the b-HB concentration was. K-one diet shows b-HB plasma levels of 300 µM, while all controls were much lower (** $p<0.01$).

What is claimed is:

1. A method for treating traumatic brain injury (TBI), comprising enterally administering to a patient suffering from TBI a nutritional composition comprising:
    (a) a lipid fraction comprising therapeutically effective amounts of
        (i) DHA and optionally EPA, and
        (ii) 1-10% wt medium-chain triglycerides based on weight of fatty acids,
    Further comprising
        (iii) saturated fatty acids (SFA) having a carbon length of 10 to 24, comprising palmitic acid in amount of more than 30 wt. % based on total SFA,
    (b) a digestible carbohydrate fraction,
    (c) a protein fraction in a weight amount of at least 15 wt. % of the total composition, comprising 50-95 wt. % casein and/or whey protein based on total protein amount, and
    (d) a dietary fibers fraction,
    wherein the composition has a glycaemic index below 69 and a ketogenic weight ratio between 1.8:1 and 2.7:1.

2. The method according to claim 1, wherein the composition has a ketogenic weight ratio between 1.8:1 and 2.5:1.

3. The method according to claim 1, wherein the composition has a ketogenic weight ratio between 2.1:1 and 2.5:1.

4. The method according to claim 1, wherein the digestible carbohydrate fraction (b) comprises 70-100 wt. % carbohydrates having a glycaemic index below 55 based on total digestible carbohydrates.

5. The method according to claim 1, wherein the protein fraction (c) comprises at least 10 wt % free leucine based on the weight of the protein fraction.

6. The method according to claim 1, wherein the medium-chain triglycerides comprise at least 2 wt % C8 and C10 medium-chain triglycerides based on weight of the fatty acids.

7. The method according to claim 1, wherein the glycaemic index of the composition is below 65.

8. The method according to claim 1, wherein the protein fraction (c) comprises branched-chain amino acids.

9. The method according to claim 8, wherein the protein fraction (c) comprises at least 10 wt % free leucine based on the weight of the protein fraction.

10. The method according to claim 1, comprising less than 2 wt % ALA based on the weight of the fatty acids.

11. The method according to claim 1, wherein the composition is tube fed.

12. The method according to claim 1, wherein the method is for treating TBI in a patient not undergoing radiotherapy and/or chemotherapy.

* * * * *